United States Patent [19]

Piana

[11] 4,268,986
[45] May 26, 1981

[54] IDENTIFICATION DEVICE

[75] Inventor: Ivana Piana, Genova-Cogoleto, Italy

[73] Assignee: Grafoplast S.A.S., Genova-Cogoleto, Italy

[21] Appl. No.: 940,860

[22] Filed: Sep. 8, 1978

[30] Foreign Application Priority Data

May 15, 1978 [IT] Italy .................... 12613 A/78

[51] Int. Cl.³ .............................. G09F 3/06
[52] U.S. Cl. .................... 40/316; 40/10 D; 40/19
[58] Field of Search ............. 40/316, 23 R, 19, 10 D, 40/317

[56] References Cited

U.S. PATENT DOCUMENTS 2,768,457  10/1956  Biek ................. 40/23 R X

FOREIGN PATENT DOCUMENTS 674239  11/1963  Canada ..................... 40/316
1115332  5/1968  United Kingdom .......... 40/316

*Primary Examiner*—Gene Mancene
*Assistant Examiner*—Wenceslao J. Contreras
*Attorney, Agent, or Firm*—Jacobs & Jacobs

[57] ABSTRACT

The invention provides an identification device in the form of a holder for symbol elements. The holder has a body and a channel portion, the body and channel portion being integral to define a one piece unit, but the body being of a relatively hard plastic and the channel portion being of a relatively soft plastic. The body portion is adapted to be springingly engaged with the object to which the holder is to be connected, while the channel portion is transparent so that the symbol elements can be seen therethrough. The holder is manufactured from a drawn composite plastic body, the body being drawn in a process similar to wire drawing.

1 Claim, 11 Drawing Figures

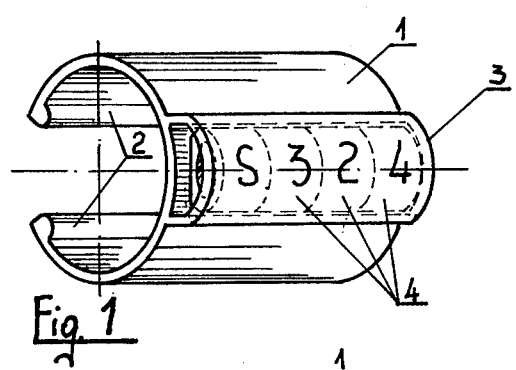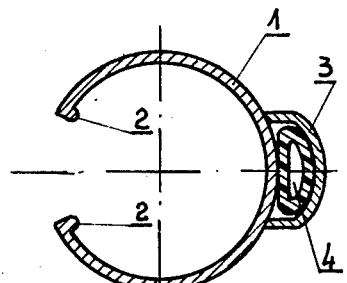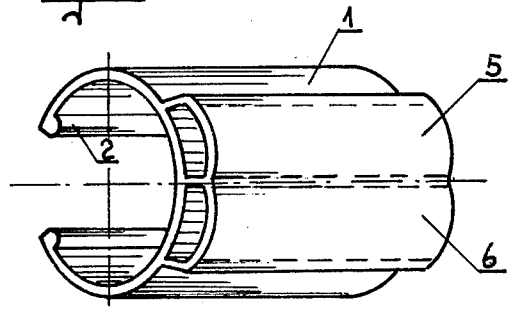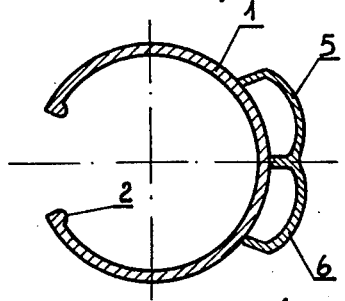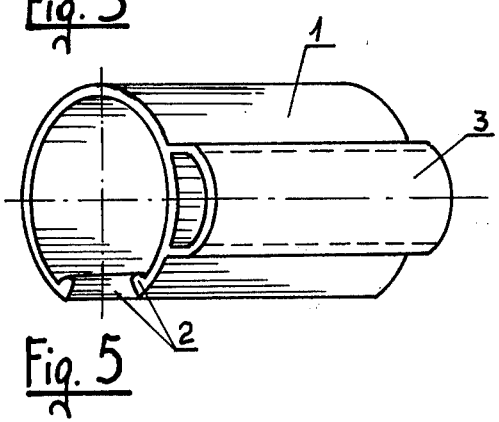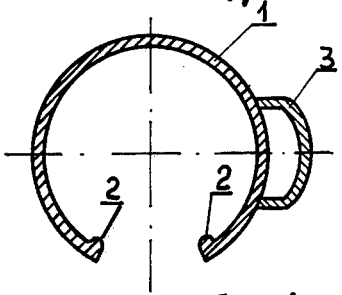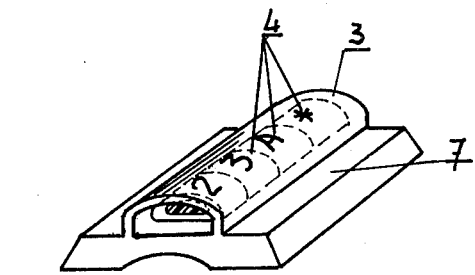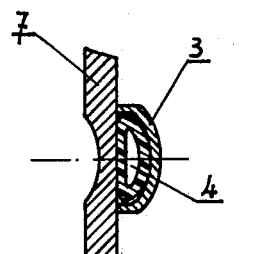

IDENTIFICATION DEVICE

This invention relates to identification devices in the form of holders for individual tabs, rings or other elements carrying symbols, letters, numbers or the like. Such elements will be referred to hereinafter as "symbol elements" when referring to these elements generally.

Identification devices in the form of holders for symbol elements are of course well known and one such holder is in the form of a sleeve for placement on an electric cable. The symbol elements used with such a holder are rings or C-shaped elements, each bearing a symbol. The elements are arranged side by side in order to compose the symbols in to the desired legend, and of course the utilisation of individual symbol elements permits easy correction and alteration. The sleeve is provided with a hollow channel for reception of the symbol elements, and naturally the channel is transparent in order that the symbol element can be viewed therethrough. The device is made of a relatively soft material, such as a soft and flexible plastic material in order to enable easy insertion of the symbol elements and to exert a sufficient degree of frictional pressure on the elements so that they do not fall out accidentally.

The utilisation of a sleeve presents the disadvantage that they must be positioned on cables before the final connection of the cables can be made, and to remove the device requires at least one cable connection to be disconnected. Additionally, each sleeve is designed for use with one cable size only, and for cables of different cross-sectional size, different sleeves must be used. It is therefore necessary to provide and keep at a users disposal, a large number of sleeves. This is not economical.

Also, it is hereto for been the case that the sleeves have been constructed of the same soft material as the alveolus channel. If, as in accordance with one embodiment of the present invention, use is made of a slotted sleeve or C-sectioned clip to provide the holder, then the use of a soft flexible material would not be entirely suitable, as it would not grip the cable with sufficient resilience to hold it thereto within use.

Holders according to the general concept of the invention can be used not only as cable markers, but also for the identification of electrical appliances as will be clear from the following.

The general object of the present invention is to provide an identification device in the form of a holder for symbol elements which can be easily connected to and disconnected from the component to be identified, yet which will hold the symbol elements as effectively as the presently known identification devices of the type to which the invention relates.

In accordance with the present invention, there is provided an identification device in the form of a holder for symbol elements comprising a body portion and a channel portion which defines with the body portion and channel for the reception of the symbol elements, the body portion being formed in a relatively hard but resilient plastics material, whilst the channel portion is formed in a relatively soft and transparent plastics material, the body portion being adapted to be held to the component to which it is to be attached by spring action; the holder comprising a one piece part consisting of the relatively hard and relatively soft materials and being obtained by drawing.

The holders are produced by cutting from the drawn composite, the holders of course being cut in the required length.

Preferably the body portion is in the form of an open or C-sectioned sleeve which can clip over a wire to be identified by the holder, the resiliency of the plastic of the body serving to hold the wire firmly to said cable. It is appreciated that with such an arrangement, it is not necessary to connect and disconnect cables for the removal and insertion of the holder.

If the holder is designed for use with an electrical appliance, the body portion will be designed accordingly. For example the body may be a generally flat component provided with one or more projecting ribs while resilient engagement in one or more grooves of the appliance to which the holder is to be attached. For example, the projecting rib may be of dove-tail section for resilient engagement with a similar sectioned groove in the appliance. The channel portion would be arranged at one side of the plate, whilst the rib or ribs would be arranged to the other side of the plate. In each case the resilience of the plastics material of the body serves for the firm holding of the holder to the appliance.

By adopting a drawing process to provide the individual holders according to the invention and in plastics materials of two different hardnesses, there is achieved a simple and effective means for producing identification holders. The utilisation of a hard plastic body and the adaptation of that body for connection to cables or electrical appliances or other components, together with a relatively soft channel portion defining the channel enabling easy insertion and removal and firm holding of the symbol elements, provides considerably advantage as compared to the Prior Art holders.

An embodiment of the invention will now be described by way of example, with reference to the accompanying drawings, wherein:

FIGS. 1 and 2 respectively show in perspective view and in transverse section a holder according to a first embodiment of the invention;

FIGS. 3 and 4 show in a similar manner to FIGS. 1 and 2, a holder according to a second embodiment of the invention;

FIGS. 5 and 6 show, similar to FIGS. 1 and 2, a third embodiment of the invention;

FIGS. 7 and 8 show, similar to FIGS. 1 and 2, a fourth embodiment of the invention;

Figure 9:
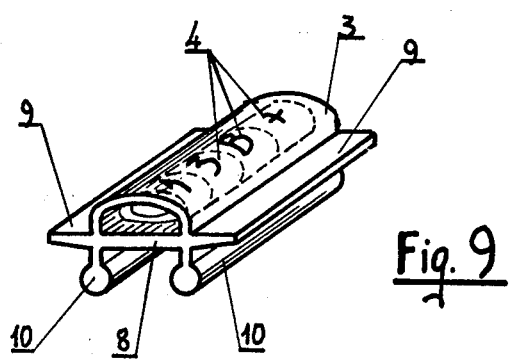
FIG. 9 shows in perspective view a holder according to a third embodiment of the invention.

Referring to FIGS. 1 and 2, the holder shown is obtained by cutting the holder of appropriate length from a drawn material, drawin in a fashion similar to wire drawing, and the holder consists of body 1 which is in the form of an open sleeve or C-section, and along the edges of the opening the body is thickened as shown by reference numeral 2. The holder comprises additionally a hollow portion 3 defining a channel in which are received the symbol elements, in this case in the form of initialled rings 4.

The body 1 is of strong and resilient plastics material, while the alveolus channel 3 is made of soft and transparent plastic and the entire holder is obtained as an unitary component by a drawing process which is similar to wire drawing.

The holder can be connected to a cable simply by pushing it laterally against the cable, which has the effect of causing the thickened ends 2 to spread and spring over the cable. The body serves for the resilient gripping of the cable thereby to ensure that the holder is held firmly thereto. The holder can be removed similarly from the cable and there is no requirement for making and unmaking cable connections for connecting the holder to and removing it from the cable.

As the holding of the holder on the cable is effected by the resilience of the body 1, it is clear that the holder can be used on cables of different sizes within a certain range.

The channel portion 3 of the holder receives the initialled rings 4, the letters of the respective rings defining the appropriate identification marking for the cable. The rings are inserted according to a well known technique by removal from suitable containers with for example, tweezers or a special tool, the tool penetrating the central hole of each ring whilst the ring is held on the tool. The rings thus can be easily inserted into and removed from the channel portion. By virtue of the fact that the channel is fabricated of soft plastic material, the introduction, fitting and holding of the rings are facilitated. At any time the rings can be removed, changed and once more inserted into the channel without coming into contact either with the sleeve or the cable.

In the embodiment of the invention shown in FIGS. 3 and 4, the holder is generally similar to the one illustrated in FIGS. 1 and 2, except that two channels 5 and 6 are defined. Such an embodiment is useful with two rows of identification indicia are required. Again, in the production of this embodiment of the invention, sleeve 1 is in strong and elastic plastic material while the channel portions 5 and 6 are in soft and transparent material. The holder is cut from a drawn plastic body, the holder being a one piece component. In the embodiment shown in FIGS. 5 and 6, the holder illustrated is generally similar to that shown in FIGS. 1 and 2, except that the opening in the sleeve is located at 90° relative to the channel portion 3, as compared to the said opening and said channel being located diametrically opposite in the FIGS. 1 and 2 embodiment.

In the embodiment shown in FIGS. 7 and 8, the body of the holder is in the form of a plate 7, and this plate is adapted to be sprung into a dove tail groove in an electrical appliance. To one side of the plate 7 is provided the channel portion 3. It will be noticed that the edges of the plate 7 are chamfered and the underside of the plate, being the side opposite from that provided with the channel portion 3, is provided with a curved groove, to enable the plate to be sprung into an appropriate groove or grooves in the electrical appliance. As with the embodiments previously described, the body 7 is in strong and elastic plastic material as it must serve the function of resiliently holding the holder to the appliance, and the channel portion 3 is a soft and transparent plastic material in order to receive the symbol elements effectively.

The holder shown in FIG. 9 again is for use in connection with electrical appliances and it comprises a plate body 8 defining two wing portions 9. The body 8 has on one side the channel portion 3 for the receipt of the symbol elements 4 and to the other side the body is provided with two longitudinal and symmetrically arranged ribs 10, at the free edge of each of which is a cylindrical enlargement as shown. The said ribs serve for the resilient connection of the holder to an appliance for an example in either of the manners indicated in FIGS. 10 and 11.

The channel portion 3 is again of soft and transparent plastic material, while the body 8 is of relatively hard and resilient plastic material, the holder being formed as a one piece unit, and being produced from being cut from a drawn body drawn in a manner similar to wire drawing.

Figure 10:
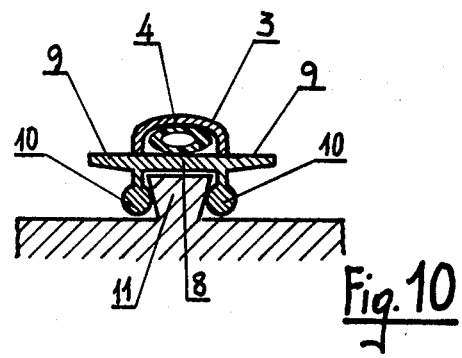
FIGS. 10 and 11 show the holder of FIG. 9 in transverse sectional elevation when mounted on an electrical appliance in two different fashions.
Figure 11:
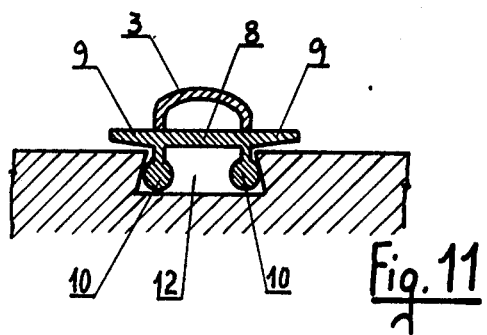

The holder shown in FIG. 9 can be easily connected to and disconnected from an electrical appliance provided with a suitable tongue or groove arrangement, the resilient connection being achieved by the use of the two ribs 10 which can either engage a dove tail projection 11 as shown in FIG. 10, or can locate in a dove tail groove 12 as shown in FIG. 11.

The holder shown in FIG. 9 may be provided with two or more alveolus channels in a manner similar to that illustrated in FIGS. 3 and 4, and additionally it is not necessary that the ends of the ribs 10 be provided with cylindrical enlargements. These enlargements could be of another section.

I claim:

1. A device for affixing identification indicia to an object comprising a body portion, said body having a substantially rectangular plate portion and a pair of longitudinally aligned, substantially straight ribs disposed on one face of said plate portion, said ribs being enlarged at their ends distal to said plate and being operable to grip said object, and a channel defining portion disposed on the other face of and integral with said body portion, said channel defining portion being operable to receive said identification indicia, said body portion being composed of a first, hard, resilient plastic material and said channel defining portion being composed of a second, soft transparent plastic material.

* * * * *